United States Patent
Subramaniam et al.

(10) Patent No.: US 9,238,608 B2
(45) Date of Patent: Jan. 19, 2016

(54) SPRAY PROCESS FOR SELECTIVE OXIDATION

(75) Inventors: Bala Subramaniam, Lawrence, KS (US); Daryle H. Busch, Lawrence, KS (US); Fenghul Niu, Lawrence, KS (US)

(73) Assignee: UNIVERSITY OF KANSAS, Lawrence, KS (US)

( * ) Notice: Subject to any disclaimer, the term of this patent is extended or adjusted under 35 U.S.C. 154(b) by 901 days.

(21) Appl. No.: 13/258,159

(22) PCT Filed: Mar. 23, 2010

(86) PCT No.: PCT/US2010/028343
§ 371 (c)(1),
(2), (4) Date: Sep. 21, 2011

(87) PCT Pub. No.: WO2010/111288
PCT Pub. Date: Sep. 30, 2010

(65) Prior Publication Data
US 2012/0022287 A1    Jan. 26, 2012

Related U.S. Application Data

(60) Provisional application No. 61/162,406, filed on Mar. 23, 2009.

(51) Int. Cl.
C07C 51/265    (2006.01)
C07C 51/255    (2006.01)
B01J 4/00    (2006.01)
B01J 10/00    (2006.01)

(52) U.S. Cl.
CPC ............... *C07C 51/255* (2013.01); *B01J 4/002* (2013.01); *B01J 10/007* (2013.01); *C07C 51/265* (2013.01); *B01J 2219/00006* (2013.01); *B01J 2219/00063* (2013.01); *B01J 2219/00065* (2013.01); *B01J 2219/00162* (2013.01)

(58) Field of Classification Search
CPC ............................. C07C 51/265; C07C 63/00
USPC .......................................................... 562/415
See application file for complete search history.

(56) References Cited

U.S. PATENT DOCUMENTS

| | | | |
|---|---|---|---|
| 4,062,654 A | 12/1977 | Shigeyasu et al. | |
| 5,087,741 A | 2/1992 | Tennant et al. | |
| 5,221,800 A * | 6/1993 | Park et al. | 562/543 |
| 5,270,019 A * | 12/1993 | Melton et al. | 422/234 |
| 5,367,096 A * | 11/1994 | Ritter et al. | 560/48 |
| 5,502,245 A * | 3/1996 | Dassel | B01J 19/24 562/413 |
| 5,939,582 A | 8/1999 | Dassel et al. | |

OTHER PUBLICATIONS

CRC Handbook of Chemistry and Physics, 71st Ed., 1990-1991, David R. Lide, Editor, pp. 6-14.*

* cited by examiner

Primary Examiner — Porfirio Nazario Gonzalez
Assistant Examiner — Kofi Adzamli
(74) Attorney, Agent, or Firm — Stinson Leonard Street LLP (57) ABSTRACT

Oxidation process can include: introducing small droplets of liquid reaction mixture having oxidizable reactant, catalyst, and solvent into a reaction zone containing oxygen and diluent gas; and oxidizing the reactant with the oxygen at a suitable reaction temperature and a suitable reaction pressure to produce an oxidized product. The liquid reaction mixture can have an aromatic feedstock having an oxidizable substituent as the oxidizable reactant. The oxidized product can include an aromatic compound having at least one carboxylic acid. For example, the aromatic feedstock can include a benzene ring having at least one oxidizable alkyl substituent, furan hetero-ring having at least one oxidizable alkyl substituent, a naphthalene poly-ring having at least one oxidizable alkyl substituent, derivatives thereof, and mixtures thereof.

26 Claims, 3 Drawing Sheets

SPRAY PROCESS FOR SELECTIVE OXIDATION

CROSS-REFERENCE TO RELATED APPLICATIONS

This application is a national phase application from PCT/US10/028343 filed on Mar. 23, 2010, which is based on and claims priority to U.S. Provisional Patent Application Ser. No. 61/162,406 filed on Mar. 23, 2009, all of which are hereby incorporated herein by reference.

This invention was made with government support under EEC-0310689 awarded by the National Science Foundation. The government has certain rights in the invention.

BACKGROUND OF THE INVENTION

Oxidation processes are common in industrial processes for preparing various types of substances. Selectivity towards and purity of the desired product, inherent safety and minimization of waste & environmental emissions are constant challenges that industrial oxidation processes face. As such, improvements in oxidation processes and the reaction systems that conduct the oxidation are continually being sought.

The catalytic liquid-phase oxidation of para-xylene to terephthalic acid (hereafter, TPA) with Co/Mn/Br based catalyst, known as the Mid-Century Process, was developed in the 1950s. In 1965, a hydrogenation step to purify TPA was added to help remove 4-carboxybenzaldehyde from the reaction product through conversion to water-soluble para-methylbenzyl alcohol and crystallization.

Another related reaction scheme produces crude TPA at relatively mild oxidation conditions with a metals/bromide catalyst system. The production of isophthalic or TPA from the corresponding xylenes has also been proposed using acetaldehyde as a promoter for the reaction. Since this process does not use bromine as a catalyst promoter, less exotic reactor materials are suitable. Another known process is characterized by the simultaneous oxidation of para-xylene and methyl para-toluate at mild temperature and comparatively low pressure without acetic acid solvent.

However, all of these processes share a common shortcoming—an inadequate or non-optimal $O_2$ mass transfer rate in the liquid phase. The mass transfer is accomplished in a stirred liquid phase reactor, wherein the air is vigorously bubbled through the liquid phase. The crude TPA solid produced via this process is separated and further purified in a subsequent stage to reduce the 4-carboxybenzaldehyde content. Further, roughly 5% of the acetic acid entering the liquid phase reactor is also oxidized (e.g., burned) in this process. Therefore, there still remains a need in the art to have an improved process that provides increased $O_2$ mass transfer rate for the production of TPA and other oxidation reactions similar to the ones discussed above.

SUMMARY

Generally, the present invention meets this and other needs through providing an oxidation system and process for selective oxidation through a spray process where each droplet can function as a micro-reactor for selective oxidation of a substrate. While the reaction proceeds within the liquid droplet, some reactions may occur in the vapor or gas phase, such that the majority of reaction occurs substantially in the liquid phase of the doplets.

In one embodiment, an oxidation process can include: introducing small droplets of a liquid reaction mixture having an oxidizable reactant, a catalyst, and a solvent into a gaseous reaction zone containing oxygen and a diluent gas; and oxidizing the reactant with the oxygen at a suitable reaction temperature and a suitable reaction pressure to produce an oxidized product. The liquid reaction mixture can have an aromatic feedstock having an oxidizable substituent as the oxidizable reactant. The oxidized product can include an aromatic compound having at least one carboxylic acid. For example, the aromatic feedstock can include a benzene ring having at least one oxidizable alkyl substituent, furan heteroring having at least one oxidizable alkyl substituent, a naphthalene poly-ring having at least one oxidizable alkyl substituent, derivatives thereof, and mixtures thereof. Examples of the aromatic feedstock include para-xylene, meta-xylene, ortho-xylene, pseudo-cumene, 3-chloro-meta-xylene, 2,6-dimethylnaphthalene, 1,5-dimethylnaphthalene, 2,7-dimethylnaphthalene, 5-hydroxymethylfurfural, furfural, 5-formylfurfural, and mixtures thereof as well as similar compounds or derivatives thereof.

In one embodiment, the aromatic feedstock can include para-xylene (p-xylene) and the oxidized aromatic compound product having at least one carboxylic acid can include terephthalic acid. Alternatively, the aromatic feedstock can include 5-hydroxymethylfurfural and the oxidized product is an aromatic compound having at least one carboxylic acid includes furan-2,5-dicarboxylic acid.

In one embodiment, the oxidized product precipitates from the droplets as a substantially pure solid material.

In one embodiment, the aromatic feedstock includes a partially-oxidized derivative of at least one member selected from the group consisting of p-toluic acid (PTA), p-tolualdehyde (p-Ta), p-hydroxymethyl benzoic acid, terephthaldehyde, 4-carboxybenzaldehyde (4-CBA), p-methylbenzyl alcohol, 5-hydroxymethylfuran-2-carboxylic acid, 2,5-diformylfuran, furfural-5-carboxylic acid, and mixtures thereof.

In one embodiment, the catalyst can include solvent-soluble compositions of palladium, platinum, cobalt, manganese, vanadium, titanium, tin, antimony, bismuth, molybdenum, and mixtures thereof.

In one embodiment, the catalyst can further include a co-catalyst dissolved in the liquid reaction mixture. For example, the co-catalyst can include manganese, bromine, or hydrogen bromide.

In one embodiment, the solvent includes acetic acid. Optionally, the acetic acid contains about 0.1 to 10% water by weight or volume.

In one embodiment, the diluent gas is inert. For example, the diluents gas can include nitrogen, carbon dioxide or a noble gas.

In one embodiment, an oxidation intermediate of the oxidizable reactant is added to the liquid reaction mixture. For example, the oxidation intermediate is selected from the group consisting of p-toluic acid, p-tolualdehyde, p-hydroxymethyl benzoic acid, terephthaldehyde, 4-carboxybenzaldehyde, p-methylbenzyl alcohol, derivatives thereof, and mixtures thereof.

In one embodiment, the liquid reaction mixture in the small droplet form is contacted with the oxygen at from about 100 to about 300° C. Also, the process can include preheating the liquid reaction mixture or the gaseous reaction zone to 100-300° C. prior to the liquid reaction mixture being sprayed into contact with the oxygen-containing gas.

In one embodiment, the liquid reaction mixture droplet is contacted with the oxygen for a time period of about 0.1 second to about 60 minutes.

In one embodiment, the reaction pressure is in a range of about 1 to about 100 atmospheres.

In one embodiment, the reaction pressure is chosen such that the reaction mixture, dominated by the solvent, begins to boil if the droplet temperature rises (due to heat evolved by the reaction) and attains a certain temperature. However, when the reaction mixture begins to boil, the latent heat of evaporation is removed from the droplet causing it to cool. In this manner, the droplet temperature can be self-controlling and stable.

In one embodiment, the process can include spraying the reaction mixture through a nozzle to form the fine mist spray in the reaction zone containing the gaseous oxidant. The nozzle can be a single fluid-type nozzle that sprays a fine mist into an oxygen-containing gas. Optionally, a gas, with or without oxygen, can be combined with the reaction mixture and sprayed through the nozzle with the reaction mixture.

In one embodiment, oxidation or combustion of the solvent or other oxidizable components (e.g., not oxidizable reactant) to CO or $CO_2$ is avoided or decreased. This can be obtained by minimizing the temperature gradients in the reactor, the pressure and by minimizing the residence time of the droplets in the reactor. In this manner, combustion of the solvent or other oxidizable components to form CO or $CO_2$ is substantially decreased.

In one embodiment, the small droplets are from 0.1 micron to about 1 mm in average diameter. Also, the small droplets can be a fine mist of droplets.

In one embodiment, an oxidation reaction system can include: a liquid reaction mixture having an oxidizable reactant, a catalyst, and a solvent; an oxidizing gas having oxygen and a diluent gas; a reaction vessel configured for retaining the oxidizing gas in a gaseous reaction zone; and a sprayer system having a nozzle configured for spraying small droplets of the liquid reaction mixture into the reaction zone.

The various components of the liquid reaction mixture can be individually supplied to the sprayer system for combination into the liquid reaction mixture and being sprayed into the reactor, or can be supplied (and optionally stored) premixed or partly premixed and partly as individual components. In like fashion, the oxidizing gas can be supplied to the reaction zone as a premix of one or more oxygen-containing gases with one or more diluent gases, or as separate oxygen-containing gas and diluent gas flows, or as individually-introduced, discrete gases.

In one embodiment, the reaction vessel can include a collection member configured for collecting an oxidized product that precipitates as a solid from the reaction zone or from the liquid droplets.

In one embodiment, the reaction vessel can include a temperature control system configured for obtaining a reaction temperature being at from about 100 to about 300° C. For example, the temperature control system can be configured to maintain a substantially uniform temperature throughout the reaction vessel.

In one embodiment, the reaction vessel can include a pressure control system configured to maintain pressure in the reaction vessel at from about 1 to about 100 atmospheres.

DETAILED DESCRIPTION OF THE PREFERRED EMBODIMENTS

Generally, the present invention is related to a system and method that employs a novel spray process for selective oxidation reactions, such as those that are catalyzed homogeneously. The spray process is configured to produce a high number of small droplets, where the droplets function as micro-reactors and the reaction substantially occurs within the droplets. However, it may be possible for some of the oxidation reaction to occur in the vapor or gas phase outside of the droplet. Also, in embodiments where the solvent is included at the base of the reactor as a bulk liquid, some oxidation may occur in the bulk liquid solvent. That is, the oxidation reaction occurs substantially within the small droplets in which the temperature rise due to heat of reaction may be controlled by evaporative cooling. The temperature can be controlled within a pressure range so that the yield losses to undesired byproducts can be minimized. For example, the system and method can be used in a novel spray process for selective oxidations including p-xylene oxidation to produce terephthalic acid as well as related oxidation reactions. Additionally, other reactants can be used in the oxidation process in order to produce desired products. Moreover, the system and process may be useful in other reactions other than oxidation reactions.

In addition to oxidation, the reactions that can be performed with the system and methods described herein can include liquid phase ozonolysis, hydrogenation reactions, carbonylation reactions, and syngas reactions. Such reaction types are known and one skilled in the art can select reagents that can be prepared into a reaction mixture that can be sprayed into a mist of small droplets for the reaction medium. These reactions can have significant improvements in yield and purity when gas-liquid mass transfer is a rate-limiting step. Syngas is a gas mixture of carbon monoxide and hydrogen, which can be produced from coal through pyrolysis to coke, followed by an exothermic reaction that forms carbon monoxide and then produces hydrogen from reacting carbon monoxide with water vapor.

For ozonolysis, the substrate can be an alkene or alkyne with ozone cleaving the substrate to produce a alcohols, aldehydes, ketones, or carboxylic acids. Hydrogenation can include substrates that have unsaturated alkyl groups that are hydrogenated by adding a pair of hydrogens in place of a double bond. Carbonylation includes reactions that introduce a carbon doubled bonded to oxygen from carbon monoxide into an organic or inorganic substrate (e.g., hydroformylation and Reppe chemistry).

Accordingly, a novel system and process is disclosed herein that can be used to perform homogeneous catalytic $O_2$ oxidations. The novel system and process can overcome $O_2$ availability limitations in the liquid phase that have limited the effectiveness and yield of prior processes, such as the Mid-Century process. The $O_2$ availability limitation has been overcome by configuring the system to spray the liquid phase (containing the substrate and catalyst dissolved in a solvent) as small droplets that each serve as micro-reactors, and where each droplet has a small enough size that allows for sufficient oxygen permeation throughout the droplet. The novel system and process can be used to oxidize various types of oxidizable substrates. The oxidizable substrates can include oxidizable moieties that can by oxidized by oxygen.

One skilled in the art will appreciate that the inventive system and process can be used beyond the context of oxidation of a liquid substrate. As such, the system and process can be used for any liquid phase (e.g., in a small droplet) homogeneous catalytic reactions invoving a gaseous reactant (e.g., oxygen) wherein the gas-liquid mass transfer is rate-limiting. The small size of the droplets significantly improves the gas-liquid mass transfer rate and thereby improves the available molecular oxygen for oxidation. Accordingly, the system and process using small droplet reactors can improve the availability of gaseous $O_2$, and thereby improve the reaction process compared to bulk liquid oxidation or large liquid volume oxidation. Improvements are also obtained from faster reaction times and tighter temperature control. The advantages of the novel system and process include high throughput, less waste, higher product purity, and improved safety as well as others.

The system and process are operated in a manner to avoid combustion of the solvent for the oxidizable reactant. The system can be controlled within a pressure range to have a selected temperature range of operation that reduces the likelihood of solvent being burned. Further, the system can be operated with the solvent for the oxidizable reactant being in equilibrium with its vapor at the reactor pressure and temperature. In this manner, the solvent in the droplets remains substantially as a saturated liquid in the reactor with little if any evaporation. If the solvent in the liquid droplets evaporates substantially, the homogeneous catalyst may precipitate, which reduces the effectiveness of the system and process. To maintain the solvent as a saturated liquid, the spray solution must be preheated to the reactor temperature prior to spraying. Further, the reactor pressure is maintained such that the temperature of the droplets do not exceed the boiling point of the solvent at that pressure.

The system and process can include spraying a liquid solvent containing dissolved oxidizable reactant and catalyst as fine droplets (e.g., as a mist) into a chamber containing $O_2$ in an inert background gas. The droplets can be formed as small as possible from a spray nozzle, such as a nebulizer, mister, or the like. The smaller droplets containing the reactant result in an increased interfacial surface area of contact between the liquid droplets and gaseous $O_2$. The increased interfacial surface area can lead to improved reaction rates and product quality (e.g., yield and purity). Also, the droplets are sufficiently small such that the $O_2$ penetrates the entire volume of the droplets by diffusion and is available at stoichiometric amounts throughout the droplet for the selective oxidation to proceed to the desired product.

In one embodiment, the system and process can be used to oxidize an oxidizable reactant without the use of a catalyst. Accordingly, non-catalytic oxidation processes using gaseous $O_2$ as an oxidant can be performed in the system described herein.

In another embodiment, the system and method increase the interfacial mass transfer area between the liquid phase and $O_2$ by spraying the reaction mixture as fine droplets into a gas having an excess of molecular oxygen. In contrast to previous oxidation systems and methods, the present invention provides the liquid phase as the dispersed phase and the gas phase as the continuous phase. Previous oxidation systems utilized liquid as the continuous phase with gas being the dispersed phase that is bubbled through the liquid. Accordingly, the novel system and method operate in an opposite manner from the previous systems and methods (e.g., Mid-Century process). In other terms, the system and method of the invention can include an oxygen gas phase as a fixed phase or batch phase. Correspondingly, the liquid droplets that are sprayed into the oxygen-containing gas environment (e.g., gaseous reaction zone) are dispersed or added continuously in the form of a spray or mist.

The small reactant droplets or mist can provide an environment (e.g., droplet) for oxidation to occur that is several hundred microns or less in diameter. If the surrounding molecular oxygen is able to instantly penetrate the droplet (i.e., if the $O_2$ diffusion time scale ($R_p^2/D_e$) is shorter than the kinetic time scale), then the oxidation can progress substantially uniformly throughout the droplet. The nearly uniform oxidation can allow the product to develop at high purity. For example, the high conversion rate of p-xylene to TPA allows the TPA product to form and precipitate out of the droplet at relatively high purity. Note that $D_e$ is the diffusivity of $O_2$ in the solvent reaction mixture and $R_p$ is the radius of the droplet. In contrast, if the droplet size is "large", the oxygen diffusion time scale ($R_p^2/D_e$) would be much longer than the kinetic time scale. In this latter suboptimal scenario, the TPA formation and precipitation commence from the outer shell of the droplet, progressing toward the inner core of the droplet. Once the solid forms near the outer layer of the droplet, the $O_2$ diffusion to the inner core can be hindered, and incomplete oxidation can result leading to a less pure TPA product, contaminated by intermediates. Thus, smaller droplets favor the production of purer product.

In order to control the reaction as described herein, the size of the droplets can be controlled. The droplets can be formed as a fine mist of individual small droplets (e.g., about 10 microns to about 100 microns), as fine droplets (e.g., about 100 microns to about 300 microns), to light droplets (e.g., about 300 microns to about 1,000 microns), as well as larger droplets. However, smaller droplets are preferred as described herein. A "mist" is considered to be a plurality of small droplets or droplets of a size commensurate with this invention, and can be formed with an atomizing nozzle.

The system and process described herein can reduce the amount of solvent (e.g., acetic acid) that is combusted/oxidized in the reaction, and therefore reduce side-products that are formed as a consequence of the burning of acetic acid. Although the surface area between acetic acid and $O_2$ is increased, the burning is not mass transfer controlled but depends on the contact time between the acetic acid and oxygen. This contact time is significantly reduced in the spray process compared to the conventional process (i.e., Mid-Century process) as the acetic acid can also be continuously removed during the spray process with minimal holdup in the reactor.

The exothermic oxidation reactions can lead to the temperature rise of reaction mixture, and thereby lead to solvent burning if the conditions of the macroscopic reactor are not properly controlled. The adiabatic temperature increase ($\Delta T_{ad}$) in the reaction mixture for total combustion of the oxidizable reactant (e.g., p-xylene) can be estimated following standard calculation procedures. It was found that the $\Delta T_{ad}$ values increases with pressure and the maximum temperature attained represents the boiling point of the solvent (e.g., acetic acid) at that pressure. The latent heat of vaporization provides enough heat capacity to absorb the heat of reaction and maintain the temperature at the phase change temperature (e.g., boiling temperature) without causing the reaction mixture to completely evaporate. As such, the operating pressure can be selected to limit the adiabatic temperature increase and prevent the temperature from increasing to or above a level where solvent burning is minimized. Higher operating pressure can lead to higher boiling points for the solvent, which in turn can cause the solvent to burn and produce side products. It was also found through calculations that the maximum local temperature of every single droplet in which reaction occurs again reaches the solvent boiling point at the given pressure.

In the commercial Mid-Century process, the $O_2$ mass transfer rate in the liquid phase is accomplished in a stirred liquid phase reactor, wherein the air is vigorously bubbled through the liquid phase. The crude TPA solid produced via this process is separated and further purified in a subsequent stage to reduce the 4-carboxybenzaldehyde content (the intermediate oxidation product which is the main impurity). Further, roughly 5% of the acetic acid entering the reactor is also oxidized (burned) in this process. Since the purity of the solid TPA product and effectiveness of the oxidation reaction can depend on the interfacial area, and thereby, droplet size, smaller droplets of reactant suspended in the gas having $O_2$ can significantly improve the oxidative reaction and product yield and purity. For example, smaller droplets lead to purer TPA products and higher TPA yields.

Figure 1:
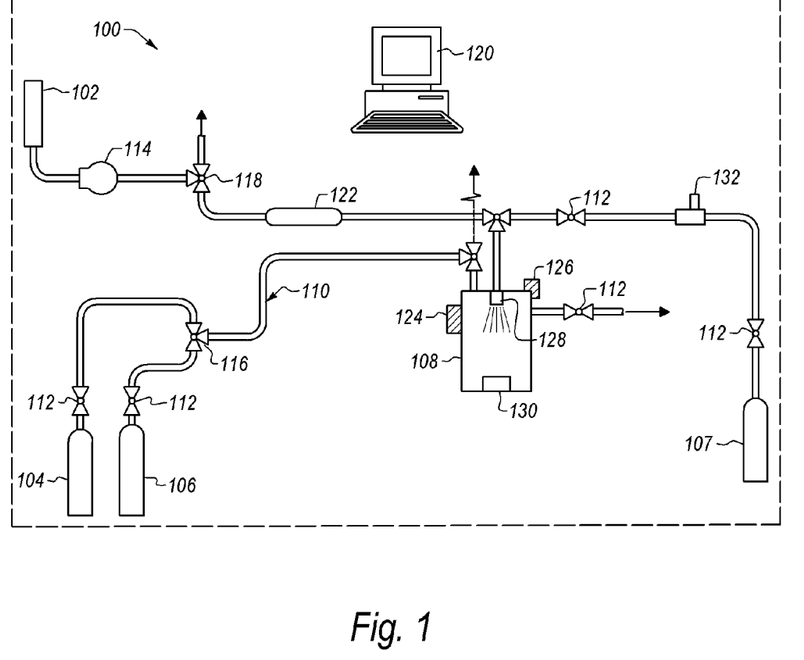
FIG. 1 is a schematic diagram of an embodiment of an oxidation reaction system.

FIG. 1 shows a diagram of an embodiment of an oxidation system 100 that can be used in the spray oxidation processes described herein. The oxidation system 100, as shown in FIG. 1, is configured for p-xylene oxidation to TPA; however, the system 100 can be used for any oxidation as described herein.

The system 100 can include a reaction mixture reservoir 102, an oxygen reservoir 104, and a diluent gas reservoir 106 in fluid communication with a reactor 108, such as through fluid pathways 110. Fluid pathways 110 are shows by the tubes that connect the various components together, such as for example, reaction mixture reservoir 102 is fluidly coupled to a pump 114, splitter 118, heater and junction 116 before being passed through the nozzle 128. Optionally, a second gas reservoir 107 having an oxygen or diluents gas can be included that can be in fluid communication with the reactor 108. The fluid pathways 110 can include one or more valves 112, pumps 114, junctions 116, and splitters 118 to allow fluid flow through the fluid pathways 110. Accordingly, the arrangement can be configured to provide for selectively transferring a reaction mixture, oxygen gas, oxygen-containing gas, inert gas, and one or more diluent gases to the reactor 108 so that an oxidation reaction can be performed as described.

Additionally, the oxidation system 100 can include a computing system 120 that can be operably coupled with any of the components of the oxidation system 100. Accordingly, each component, such as the valves 112 and/or pumps 114 can receive instructions from the computing system 120 with regard to fluid flow through the fluid pathways 110. General communication between the computing system 120 and oxidation system components 100 is represented by the dashed-line box around the oxidation system 100. The computing system 120 can be any type of computing system ranging from personal-type computers to industrial scale computing systems. Also, the computing system can include a storage medium, such as a disk drive, that can store computer-executable instructions (e.g., software) for performing the oxidation reactions and controlling the oxidation system 100 components.

The fluid pathway 110 that fluidly couples the reaction mixture reservoir 102 may include a heater 122 as shown. The heater 122 can pre-heat the reaction mixture to a desired temperature before being introduced into the reactor 108. While not shown, the fluid pathway 110 that fluidly couples any of the gas reservoirs can similarly include a heater to heat the gases to a temperature before being introduced into the reactor 108. Any of the heaters 122 can be operably coupled with the computing system 120 so that the computing system 120 can provide operation instructions to the heater 122, and/or the heater 122 can provide operation data back to the computing system 120. Thus, the heaters 122, as well as any of the components, can be outfitted with data transmitters/receivers (not shown) as well as control modules (not shown).

The fluid pathways 110 can be fluidly coupled with one or more nozzles 128 that are configured to spray the reaction mixture (and optionally including the oxygen-containing and diluent gases from 104 and 106 and/or the gases from reservoir 107, if nozzles 128 are employed for injecting both gases and liquids or a mixture of gases and liquids) into the reactor 108. The nozzles 128 in any such arrangements can be configured to provide liquid droplets of the reaction mixture at an appropriately small size that allows for the oxidation reaction to occur with limited evaporation of the solvent. The nozzles 128 can spray the reaction mixture into a plurality of droplets within a size range that is desired. While FIG. 1 shows the nozzle 128 to be pointed downward, the nozzle 128 in fact can be in any orientation and a plurality of nozzles 128 can be configured into any arrangement. Similarly, the droplets may be formed by other methods such as ultrasound to break up a jet of the spray solution.

The reactor 108 can include a tray 130 that is configured to receive the oxidation product. As the oxidation product is formed, it can fall out of the droplets, such as by precipitation, and land on the tray 130. Also, the tray 130 can be a mesh, filter, and membrane or have holes that allow liquid to pass through and retain the oxidation product. Any type of tray 130 that can catch the oxidation product can be included in the reactor 108.

The reactor 108 can be outfitted with a temperature controller 124 that is operably coupled with the computing system 120 and can receive temperature instructions therefrom in order to change the temperature of the reactor 108. As such, the temperature controller 124 can include heating and/or cooling components as well as heat exchange components. The temperature controller 124 can also include thermocouples to measure the temperature and can provide the operating temperature of the reactor 108 to the computing system 120 for analysis.

The reactor 108 can be outfitted with a pressure controller 126 that is operably coupled with the computing system 120 and can receive pressure instructions therefrom in order to change the pressure of the reactor 108. As such, the pressure controller 126 can include compressors, pumps, or other pressure modulating components. The pressure controller 124 can also include pressure measuring devices to measure the pressure of the reactor and can provide the operating pressure of the reactor 108 to the computing system 120 for analysis.

Additionally, the oxidation system 100 can include a mass flow controller 132 that is fluidly coupled to the reaction mixture reservoir 102 and the second gas reservoir 107. The mass flow controller 132 can be useful during an oxidation process where the reaction mixture is charged with gas (e.g., oxygen, oxygen-containing gas, inert gas, and/or diluents gas) before being sprayed from the nozzle 128. The mass flow controller 132 can be configured such that the computing system 120 can modulate the amount of gas charged into reaction mixture, which in turn can modulate the size of the droplets that are sprayed from the nozzle 128. Thus, the mass flow controller 132 can be used to feed the energizing gas into the liquid reaction mixture and then through the nozzle 128 to assist in forming small droplets.

The oxidation system 100 of FIG. 1 can include components that are made of standard materials that are commonly used in storage containers, storage tanks, fluid pathways, valves, pumps, and electronics. Also, the reactor and the nozzles can be prepared from oxidation resistive materials. For example, the reactor can include a titanium pressure vessel equipped with a heater, a standard solution pump, and a ceramic spray nozzle (e.g., non-corrosive material). An high pressure liquid chromatography (HPLC) solution reciprocating pump or a non-reciprocating piston pump are available to feed the reaction mixture through the nozzle. The reaction mixture can be pre-heated to the reaction temperature by a tubular heater associated with the reactor.

Also, the reactor can include liquid solvent in a predetermined amount before receiving the reaction mixture and/or gases. The liquid solvent can be the same solvent that is included in the reaction mixture, which is heated to a temperature at or about the boiling point of the solvent at a desired pressure. The temperature/pressure can allow for the solvent to boil so that there is solvent vapor within the reactor before conducting the oxidation reaction. The amount of solvent that is boiled or vaporized can be allowed to reach equilibrium or a saturate state so that the liquid solvent with the reaction mixture has less potential to vaporize. This reactor condition can be useful to inhibit the reaction mixture droplets from vaporizing, and also inhibits the catalyst or oxidizable reactants from precipitating from the droplets as the solvent evaporates. As such, including liquid solvent within the reactor for vaporization and solvent liquid-vapor equilibrium can improve the oxidation reaction efficiency and produce a higher reaction rate as well as increased oxidation product purity.

In one embodiment, when the reactor is stabilized at the set-point temperature and pressure, a charge gas (e.g., $N_2$ gas) can be introduced into the reactor via a mass flow controller, a pre-heater (an oil bath), and a mixing tee. The reaction mixture can also be pumped at a predetermined flow rate through the mixing tee and the capillary nozzle. The charge gas serves to break up the components in the reaction mixture, causing it to be sprayed as a fine mist into the reactor where it meets the preheated molecular oxygen and diluents gas mixture (e.g., $O_2/N_2/CO_2$ mixture).

In one embodiment, the present invention can include a reaction system for use in a spray-based catalytic oxidation reaction process. The reaction system can include: a liquid reaction mixture comprising a reactant, a catalyst composition, and a solvent; an oxidizing gas having oxygen and an inert diluent gas; a reaction vessel configured for retaining the oxidizing gas in a gaseous reaction zone; and a sprayer system having a nozzle configured for spraying fine droplets of the liquid reaction mixture into the reaction zone (e.g., gaseous reaction zone). The reaction vessel can include titanium. The sprayer system can include a ceramic capillary tube and an inert nozzle, such as stainless steel or titanium or other alloys. The reactant can have at least one oxidizable substituent. Additionally, the reaction vessel can include a member configured for collecting an oxidized product that precipitates. The system can include other features, compositions, or the like as described herein. Further, the reactor can also be operated continuously such that the spray and the gas stream containing the oxidant are admitted at a constant rate into the reactor while the product stream is withdrawn continuously while maintaining the reactor pressure and temperature.

In one embodiment, the system can use a reactor and spray nozzles that are configured to be inert during the reaction process. As such, the reactor and spray components can be prepared from stainless steel, titanium, or the like. Titanium can be preferred over stainless steel, especially for the nozzles. Also, inert polymeric components or ceramic components can be used in the reactor system. The number of nozzles can be modulated depending on the desired production rate. Also, the nozzles can be configured to change the droplet size as needed or desired depending on the reaction rate of the particular reaction being conducted. Nebulizing sprayers that mist the reactant droplets can provide for increased interfacial surface areas for enhancing the reaction effectiveness.

Additionally, the reaction system can be equipped with heat transfer devices that can draw heat away from the reaction. The increased reaction/production rate may also result in increased heat generation from the reaction. Accordingly, the reaction system can include a temperature control system to maintain the temperature within a suitable range. The temperature control system, which can include heat transfer devices, can remove the heat from the reaction in order to prevent unwanted temperature increases and inhibit solvent (e.g., acetic acid) burning. For example, the heat transfer device or temperature control system can include temperature sensors, temperature controllers, and cooling coils or the like.

As provided herein, experimental data clearly shows that the spray process with small droplets of reactant being sprayed or blown into an oxygen-containing gas produces a purer TPA product when compared to the conventional process. Accordingly, the same spray process with small droplets can be used for producing other products with increased purity compared to mechanical stirring methods. Thus, the novel spray system and process can be applicable for other classes of reaction wherein gas/liquid interfacial area can be be maximized to increase reaction rates and/or product selectivity (e.g., increased purity and yield).

The system and process provides an oxidation reaction that oxidizes a reactant within a small droplet. The oxidation reaction can be performed with or without a catalyst depending on the substrate being oxidized. As such, the process can include introducing small droplets of a liquid reaction mixture having an oxidizable reactant, a catalyst, and a solvent into a gaseous reaction zone containing oxygen and a diluent gas. The oxidizable reactant can then be oxidized by reacting with the oxygen in the diluents gas, where the reaction can be performed at a suitable reaction temperature and a suitable reaction pressure to produce an oxidized product.

In one embodiment, a process for the production of at least one aromatic carboxylic acid can include: feeding a liquid reaction mixture comprising an aromatic feedstock, a catalyst composition, and a solvent in the form of a fine mist spray into a gaseous reaction zone containing oxygen, an inert diluent gas, and solvent vapor; and causing or allowing the aromatic feedstock and oxygen to react together at a suitable reaction temperature and a suitable reaction pressure to produce an oxidized product including the at least one aromatic carboxylic acid group.

More broadly, an aromatic feedstock can be selected from the group consisting of benzene having at least one oxidizable alkyl substituent, naphthalene having at least one oxidizable alkyl substituent, and mixtures thereof. For example, the aromatic feedstock can be selected from the group consisting of para-xylene, meta-xylene, ortho-xylene, pseudo-cumene, 3-chloro-meta-xylene, 2,6-dimethylnaphthalene, 1,5-dimethylnaphthalene, 2,7-dimethylnaphthalene, and mixtures thereof. In a specific example, the aromatic feedstock is para-xylene and the oxidized product is terephthalic acid, which includes at least one aromatic carboxylic acid.

In one embodiment, the oxidation product precipitates from the mist droplets as a substantially pure solid material. For example, the terephthalic acid precipitates from the mist droplets as a substantially pure solid material. Accordingly, the system can include a tray, net, sieve, or other member configured to catch and retain the oxidized product that precipitates from the droplets. The tray can also help separate the oxidized product from the solvent or side products as the product is a precipitate that collects on the tray while the solvent, reactants, or side products are soluble and do not precipitate.

In a variation, the aromatic feedstock can include a partially oxidized derivative of the aromatic substance. The partially-oxidized derivative can include at least one member selected from the group consisting of p-toluic acid, p-tolualdehyde, p-hydroxymethyl benzoic acid, terephthaldehyde, 4-carboxybenzaldehyde, p-methylbenzyl alcohol, and mixtures thereof. Also, the aromatic feedstock can include an un-oxidized and partially oxidized substance. Thus, for example, in one embodiment, an oxidation intermediate of the oxidized reactant can be included in the reaction mixture. For example, the oxidation intermediate from oxidizing the corresponding aromatic feedstocks can be selected and added to the liquid reaction mixture, including p-toluic acid, p-tolualdehyde, p-hydroxymethyl benzoic acid, terephthaldehyde, 4-carboxybenzaldehyde, p-methylbenzyl alcohol, and mixtures thereof.

In one embodiment, the catalyst can be selected from the group consisting of solvent (e.g., acetic acid) soluble compositions of palladium, platinum, cobalt, manganese, vanadium, titanium, tin, antimony, bismuth, molybdenum and mixtures thereof. As such, the catalyst can include cobalt dissolved in the liquid reaction mixture. Optionally, the catalyst can further include a co-catalyst comprising manganese dissolved in the liquid reaction mixture. In another option, the catalyst composition is dissolved in the liquid reaction mixture and further comprises bromine or hydrogen bromide.

The solvent for the system and process can be any organic solvent that can dissolve the oxidizable reactant and in which the catalyst can be dissolved and retained as the substantially pure oxidized product precipitates from the liquid reaction mixture and is recovered. Examples of suitable organic solvents include formic acid, acetic acid, propionic acid, and similar longer chain acids.

In one embodiment, the solvent includes acetic acid. Optionally, the acetic acid contains some water. For example, the solvent, such as acetic acid, can include from about 0.1% to 10% water, from about 0.5% to about 5%, or from about 1% to about 3% water by weight or volume.

In one embodiment, the macroscopic reaction vessel can include molecular oxygen in a diluent gas. Optionally, the diluent gas can be substantially inert. Examples of inert diluents gases can include the noble gases, nitrogen, or carbon dioxide.

In one embodiment, an oxidation intermediate of the oxidized reactant can be included in the reaction mixture. For example, the oxidation intermediate can be selected from the group consisting of p-toluic acid, p-tolualdehyde, p-hydroxymethyl benzoic acid, terephthaldehyde, 4-carboxybenzaldehyde, p-methylbenzyl alcohol, and mixtures thereof are added to the liquid reaction mixture.

In one embodiment, the liquid reaction mixture in the form of a fine mist spray is contacted with the oxygen in the gaseous reaction zone with the reaction temperature being in a range of about 100-300° C., about 170-230° C., or about 190-210° C. when the solvent is acetic acid at a pressure of from 1 atmosphere to about 100 atomspheres (or about 5-75 bars, and 10-60 bars). For example, at about 10-15 bars acetic acid boils below 250 degrees C., which keeps the temperature constant below 250 degrees C. Other solvents can be used and the boiling temperature of the solvent at a given pressure can be calculated to provide appropriate operating ranges and control limits to ensure sufficient solvent remains in liquid form. The liquid reaction mixture and/or gas can be preheated prior to being introduced into the gaseous reaction zone.

In one embodiment, the liquid reaction mixture in the form of a fine mist spray is contacted with the oxygen in the reaction zone for a time period of about 0.1 seconds to about 60 minutes, about 0.2 second to about 15 minutes, or about 0.3 second to about 5 minutes.

In one embodiment, the reaction pressure is in a range of about 1 to about 100 atmospheres, about 1 to about 40 atmospheres, or about 1 to about 25 atmospheres.

In one embodiment, the liquid reaction mixture and the reactive molecular oxygen have a contact time such that burning of the solvent or other oxidizable components to form CO or $CO_2$ is substantially eliminated. Also, the temperature, pressure, and volume of the liquid droplet can be controlled to reduce burning or oxidizing the solvent.

It has been found that a tighter temperature range and less temperature gradient within the reactor can provide for better yield and purity of the oxidation product. If a temperature gradient exists, it can cause the solvent (e.g., acetic acid) in vapor to not reach saturation due to a small temperature drop. Thus, the concentration of solvent in the vapor phase drops so that when the reaction mixture having the solvent is sprayed as droplets into the reactor, the solvent from the droplets can enter the reaction zone that has a lower temperature than the boiling point of the solvent. This can cause some solvent in the droplets to vaporize, which in turn can cause the catalyst to precipitate out. For example, acetic acid can be included in the reactor vessel, and then reactor vessel is pre-heated so that the acetic acid vapor forms at about 200° C., and then the reactor vessel is pressurized with an oxygen/diluents gas mixture before the reaction mixture is sprayed as droplets into the reactor vessel.

In one embodiment, the system and process can be used for the production of at least one furan-based carboxylic acid. As such, the reaction process can include: feeding a liquid reaction mixture comprising a furan-based feedstock, a catalyst composition, and a solvent in the form of a fine mist spray into a gaseous reaction zone containing oxygen, an inert diluent gas, and solvent vapor; and causing or allowing the furan-based feedstock to react with the oxygen at a suitable reaction temperature and a suitable reaction pressure to produce an oxidized product to form at least one furan-based carboxylic acid. The furan-based feedstock can be selected from the group consisting of furans having at least one oxidizable alkyl substituent. For example, the furan-based feedstock can be selected from the group consisting of 5-hydroxymethylfurfural, furfural, 5-formylfurfural, and mixtures thereof. In another example, the furan-based feedstock comprises 5-hydroxymethylfurfural and the furan carboxylic acid is furan-2,5-dicarboxylic acid.

In one embodiment, the furan-based feedstock can include a partially oxidized derivative of at least one member selected from the group consisting of 5-hydroxymethylfuran-2-carboxylic acid, 2,5-diformylfuran, furfural-5-carboxylic acid, and mixtures thereof. Also, an oxidation intermediate selected from the group consisting of 5-hydroxymethylfuran-2-carboxylic acid, 2,5-diformylfuran, furfural-5-carboxylic acid, and mixtures thereof can be added to the liquid reaction mixture.

In one embodiment, the feedstock can include 2,5-dimethyl furan (DMF), which can be oxidated to 2,5-dimethyl-2,5-dimethoxydihydrofuran.

Hydroxymethylfurfural (HMF) can also be a feedstock. HMF can be converted into a variety of derivatives, many of which are currently or are quickly becoming commercially valuable. Oxidation of HMF can produce oxidation products including DMF, diformyl furan (DFF), hydroxymethyl furan carboxylic acid (HMFCA), formylfuran carboxylic acid (FFCA), and furandicarboxylic acid (FDCA). Uses for these oxidation products include but are not limited to adhesives, sealants, composites, coatings, binders, foams, curatives, monomers and resins. The DMF oxidation product can be used as an alternative fuel.

Optionally, a gas, such as an oxygen-containing gas and/or an inert gas or diluents gas, can be combined with the reaction mixture prior to being sprayed. There are various configurations that are possible for the spray process and mixing gas with the liquid reaction mixture prior to spraying. Some examples can include pressure-swirl nozzles, impact-type nozzles, gas-assist nozzles, diluent supplied as gas shroud via a nozzle to minimize nozzle overheating/carbonization/thermal stresses, as well as other types of nozzles and liquid-gas mixing and spraying.

In one embodiment, the liquid droplets for formed within the reaction vessel from a liquid mixture that is at the base of the reaction vessel. Also, a thin film or small diameter continuous flow stream can be introduced into the reaction vessel where oxygen is blown through the thin film or small diameter continuous flow stream.

In one embodiment, the reaction vessel can be evacuated or flushed and filled with a diluents gas. Oxygen can then be introduced with the liquid reaction mixture together or separately.

EXPERIMENTAL

A reaction system substantially as shown in FIG. 1 was utilized for an oxidation reaction. The maximum operating pressure for the spray reactor unit is 2500 psi at a temperature of 300° C. However, the spray reactor can be configured to operate at any pressure or temperature. The reactor unit is a titanium reactor equipped with silica capillary nozzles or commercial spray nozzles. Two reactors, 40 mL (1.16" ID×1.6" height) and 700 mL (3" ID×6" height), have been successfully used, and as such, volumes at 1 L, 10, L, 100 L, or larger are likely to also be effective. The larger reactors can provide a longer residence time for the droplets/particles to descend before reaching the acetic acid dominated liquid phase at the bottom of the vessel, which can be beneficial for increasing yield and conversion. The inner diameter of the tested silica capillary nozzles ranged from 50 to 180 microns. $N_2$ or other inert gas can be used for leakage testing and as the energizing gas or diluents gas. Also, $CO_2$ was used as an inert gas inside the reactor to reduce vapor phase flammability; however, other inert gases can be used, such as noble gases.

A mass flow controller can be used to feed the energizing gas through the capillary nozzle. An HPLC pump or a syringe pump (e.g., used mostly to avoid pulsating spray) are available to feed the solution through the nozzle. The spray solution can be pre-heated to the reaction temperature by a tubular heater.

For a typical spray oxidation experiment, the spray solution can be prepared as described herein. The catalytic components (2.5 mM Co as cobalt acetate, 2.5 mM Mn as Mn acetate and 6.5 mM Br as HBr) can be dissolved in a liquid phase containing 2.7 wt % p-xylene, 6.9% water and 90.43% acetic acid. A known amount of acetic acid (4 mL) can be pre-loaded in the reactor and preheated to the reaction temperature. In this manner, the spray can enter a vapor phase saturated with acetic acid at the reaction temperature and pressure, thereby avoiding acetic acid evaporation from the spray droplets that would lead to unwanted catalyst precipitation. The whole system can be leak-tested using $N_2$. Following leak testing, the reactor can be pressurized with $CO_2$ to 103 psi. The vessel can be heated by a heating tape/band or the like to the chosen operating temperature. When the temperature is obtained, $O_2$ can be added to the final pressure at equal partial pressures.

A LabView program or other like software can be used to monitor, control, and record process temperatures (e.g., preheater, reactor) and pressure, or other reaction conditions. When the reactor is stabilized at the set-point temperature, $N_2$ gas can be introduced into the reactor via a mass flow controller, a pre-heater (an oil bath), and a mixing tee. The spray solution can be pumped at a predetermined flow rate through the mixing tee and the capillary nozzle. The flowing $N_2$ serves to break up the solution stream, causing it to be sprayed as a fine mist into the reactor where it meets the preheated $O_2/N_2/CO_2$ mixture. The p-xylene (or other reactant) in the small droplets reacts with $O_2$ in the reactor to form TPA (or other corresponding product). After a predetermined amount of solution is fed into the reactor, the solution pump can be stopped. The solution in the feed line between the 3-way valve and the tee can be purged out through the 3-way valve. The $N_2$ flow can be stopped and the reactor can be allowed to cool by turning off the heaters. When the reactor has cooled to room temperature, the solid TPA (or other product) and the solution can be removed from the reactor. The solids can be filtered from the solution, dried in an oven and weighed. The solid residue in the reactor can be recovered by washing with DMSO. The purity of TPA can be analyzed by HPLC and/or UV spectrophotometer. The wash liquid was also analyzed by HPLC.

Alternatively, the reactor can be fitted with mesh or sieve membranes at various sizes that catch the precipitated product and allow the solution to fall through.

p-Xylene Oxidation to TPA Using Spray Method

Experimental conditions: 40 mL bomb reactor, 100 μm silica capillary nozzle, 0.6 mL/min of solution, 54 scc/min of $N_2$. The reaction temperatures and pressures are shown in the following table. Before the spray was introduced, the vessel was loaded with 4 mL of acetic acid, and gas composed of 50% $CO_2$ and 50% $O_2$.

Experimental results: The experimental results using the small reactor and HPLC pump are shown in Table 1, where $X_{p-x}$ is the conversion of p-xylene, $Y_{TPA}$ is the yield of terephthalic acid, $Y_{4-CBA}$ is the yield of the 4-carboxybenzaldehyde byproduct, $Y_{PTA}$ is the yield of p-toluic acid, $Y_{P-Ta}$ is the yield observed of p-tolualdehyde and $OD_{340}$ is the optical density of the desired TPA product determined by UV-Vis.

TABLE 1

First Spray Reaction Results Using Small Titanium Reactor and HPLC Pump

| Spray solution, min | P psi | T °C. | $X_{p-x}$% | $Y_{TPA}$% | $Y_{4-CBA}$% | $Y_{PTA}$% | $Y_{P-Ta}$% | TPA Purity* % | $OD_{340}$ |
|---|---|---|---|---|---|---|---|---|---|
| 5 | 652-960 | 200 | >99 | 70.0 | 1.8 | 7.5 | 2.1 | 99.0 | — |
| 15 | 676-1284 | 200 | >99 | 92.7 | 0.6 | 2.6 | 0.7 | 99.4 | 0.038 |
| 15 | 463-1000 | 200 | 96.9 | 82.1 | 1.6 | 3.8 | 0.7 | 99.4 | n.d. |
| 15 | 663-1345 | 225 | >99 | 90.8 | 0.5 | 2.2 | 1.1 | 99.4 | 0.042 |
| 10 | 612-963 | 225 | >99 | 94.9 | 0.6 | 1.9 | 1.0 | 99.5 | 0.066 |
| 10 & 4 hrs post reaction | 516-915 | 225 | >99 | 94.5 | 0.1 | 1.6 | 0.7 | 99.8 | n.d |
| 10 | 760-1260 | 225 | >99 | 88.3 | 0.5 | 2.4 | 0.5 | 99.9 | n.d |
| 10 | 720-1196 | 225 | >99 | 90.6 | 0.8 | 2.7 | 0.6 | 99.9 | n.d |
| 10 | 856-1346 | 235 | >99 | 82.2 | 0.7 | 2.1 | 0.7 | 99.9 | n.d |

*purity (wt. %) of the recovered solid product

The solid TPA products from all experiments listed in Table 1 have 99+% purity. The use of higher temperature (225° C.) slightly reduces the intermediate product yields. At 225° C., allowing a further four hours of reaction time post-spraying further reduces the intermediate products and increases TPA purity suggesting continued oxidation of the intermediate products in the liquid phase. The TPA product is a white crystalline solid. The optical density ($OD_{340}$) values confirm the high purity of the solid TPA product.

Large Titanium Reactor (700 mL) and a MicroWhirl® Spray Nozzle

To increase the throughput of the reaction liquid, a high capacity pressure swirl-type spray nozzle constructed according to U.S. Pat. No. 7,198,201 (MicroWhirl® spray nozzle, BETE Fog Nozzle, Inc., Greenfield, Mass. 01301) was acquired and tested. This new nozzle requires more than a 10× increase in liquid flow rate (compared to the capillary nozzle) to generate a fine spray mist but without the need for an energizing gas. The minimum spray requirement is roughly 35 mL/min of liquid. Roughly, 105 mL of liquid solution was sprayed in each experiment at a spray rate of 35 mL/min. A larger capacity reactor (700 mL) was also used to handle the increased liquid holdup. The other experimental conditions and results are shown in Table 2. Note that the catalyst concentration is 5 times greater than that employed in Table 1 experiments.

At 225° C. (Entries P32 & P33), the yields of the TPA and the intermediate products are lower than those obtained with the capillary nozzle in the small reactor. However, the TPA product purity is of similar magnitude. The relatively large material balance deficit (obtained by adding all the intermediate product yields and comparing with the p-X conversion) is attributed to the enhanced burning facilitated by the higher catalyst concentration. Lower temperatures (200 and 180° C.) provide equally high p-X conversions and TPA product purity but with much less material balance deficit. This suggests that lower temperatures reduce burning of the reactant and/or intermediate products. These results clearly show that (a) the MicroWhirl® nozzles are capable of providing much higher TPA production capacity, and (b) there is room to further optimize the spray process to improve conversion and product yields while minimizing burning.

To obtain purer TPA (>99.9%) in one step, the heating of the 700 mL reactor was redesigned to minimize axial temperature gradients in the reactor so that the reaction occurs in the different droplets at a substantially uniform temperature. The improvements included increasing the pre-heater bath temperature, adding two heaters with independent control, and a profile thermocouple, (containing four thermocouples spaced 1.5" apart) to measure the temperature at various axial locations in the reactor. The experimental conditions and results are shown in Table 3.

TABLE 2

Spray Reactor Results Using 700 mL Reactor

| Run # | Spray time (min) | Initial Pressure (bar) | p-X added (mL) | T (° C.) | $X_{p-x}$ (%) | $Y_{TPA}$ (%) | $Y_{4-CBA}$ (%) | $Y_{PTA}$ (%) | $Y_{P-Ta}$ (%) | TPA Purity** (%) | $OD_{340}$ |
|---|---|---|---|---|---|---|---|---|---|---|---|
| ⅜ mm BETE MicroWhirl nozzle, 35 mL/min of solution, No N2, Co = 12.5 mM, Mn = 12.5 mM, Br = 32.5 mM, p-x = 0.26M, 812 G 1400 psi ||||||||||||
| P32 | 3 | 60 | 3.39 | 225 | >99 | 82.9 | 0.4 | 0.74 | 0 | 99.8 | n.d. |
| P33 | 3 | 60 | 3.39 | 225 | >99 | 85.5 | 0.47 | 1.75 | 0.31 | 99.9 | n.d. |
| P34 | 3 | 60 | 3.39 | 200 | >99 | 92.5 | 0.04 | 1.4 | 0 | 99.6 | 0.046 |
| P35 | 3 | 60 | 3.39 | 200 | >99 | 92.4 | 0.6 | 2.2 | 0.3 | 99.5 | 0.016 |
| P36 | 3 | 30 | 3.39 | 200 | >99 | 94.0 | 0.6 | 1.7 | 0.2 | 99.6 | 0.064 |
| P37 | 3 | 30 | 3.39 | 180 | >99 | 94.6 | 0.7 | 1.6 | 0.2 | 99.5 | 0.025 |
| P38 | 3 | 30 | 3.39 | 180 | >99 | 94.8 | 0.7 | 1.7 | 0.2 | 99.5 | n.d. |

**purity (wt. %) of the recovered solid product

TABLE 3

Results from 700 mL Spray Reactor with Tighter Temperature Control

| Run # | Spray time (min) | Initial Pressure (bar) | p-X added (mL) | T* (° C.) | $X_{p\text{-}x}$ (%) | $Y_{TPA}$ (%) | $Y_{4\text{-}CBA}$ (%) | $Y_{PTA}$ (%) | $Y_{P\text{-}Ta}$ (%) | TPA Purity** (%) | $OD_{340}$ |
|---|---|---|---|---|---|---|---|---|---|---|---|
| | | | | | Co = 12.5 mM, Mn = 12.5 mM, Br = 32.5 mM, p-x = 0.26M | | | | | | |
| 1 | 3 | 30 | 3.39 | 200 | >99 | 95.1 | 0.22 | 1.34 | 0.26 | No detectable impurities*** | 0.051 |
| 2 | 3 | 30 | 3.39 | 200 | >99 | 98.3 | 0.22 | 0.86 | 0.17 | No detectable impurities | 0.060 |
| 3 | 3 | 30 | 3.39 | 200 | >99 | 95.7 | 0.15 | 0.54 | 0.13 | No detectable impurities | 0.027 |

*T is the set temperature for $T_1$ and $T_3$. The temperatures are defined in the FIG. 2.
**Purity (wt. %) of the recovered solid product.
***No 4-CBA or other impurities peaks are detected based on HPLC analysis An HPLC analysis was conducted with a Shimadzu CT0/20 A/20 AC with dual wavelength detector LC-20AT, and a C18 reverse phase column (Waters ODS-2 5u column; 250 mm×4.6 mm: purchased from Alltech). The mobile phases included: Aqueous phase: 0.1 (wt %) phosphoric acid solution-Solvent A: and Organic phase: Acetonitrile: methanol=7/2 (by volume)-Solvent B. The measurements were made at wavelengths: 254 nm and 215 nm (dual wavelength mode), with an oven temperature of 40° C., and an injected volume injected of 15 μL.

From Table 3, it can be seen that the yield of TPA is over 95% and the optical density is lower. The impurities in the solid TPA are not detectable by HPLC analysis. Based on confirming that 100 ppm of 4-CBA is detectable in the TPA product by HPLC analysis, it is concluded that the 4-CBA content (the usual impurity) in the TPA product is <100 ppm. In other words, the TPA purity in the product is at least 99.99 wt %.

Figure 2A:
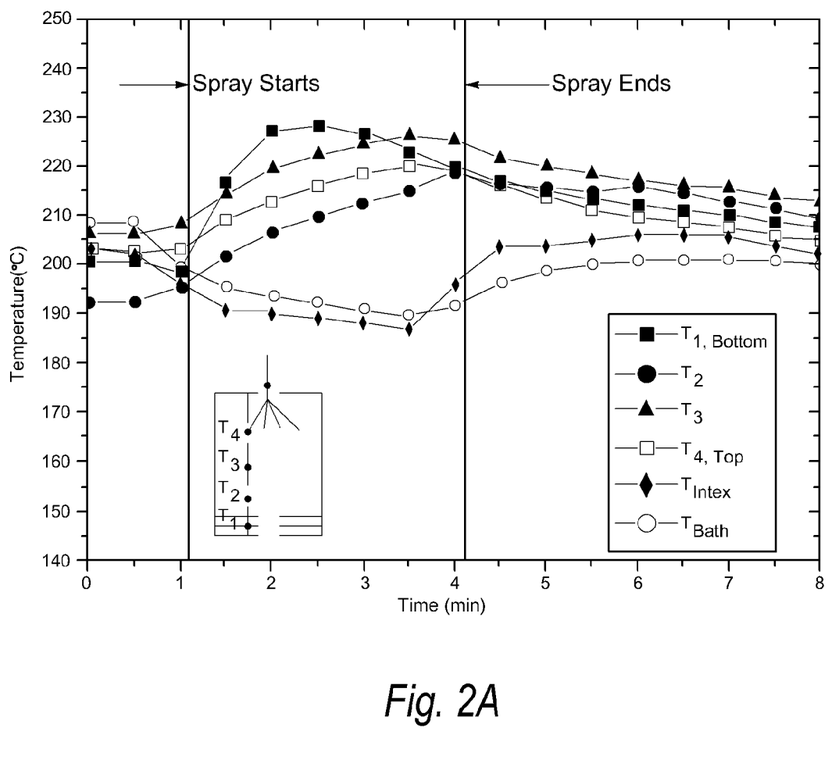
FIG. 2A is a graph of a temperature profile obtained with an oxidation reaction system having substantially uniform temperature across a cross-sectional profile of the reaction vessel.

A typical temperature profile following the heater redesign and substantially constant temperature profile in the reaction vessel is shown in FIG. 2A. Based on comparison with the temperature profile obtained without the heater redesign (FIG. 2B), it is clear that the temperature gradients were indeed significantly minimized in the redesigned reactor.

Figure 2B:
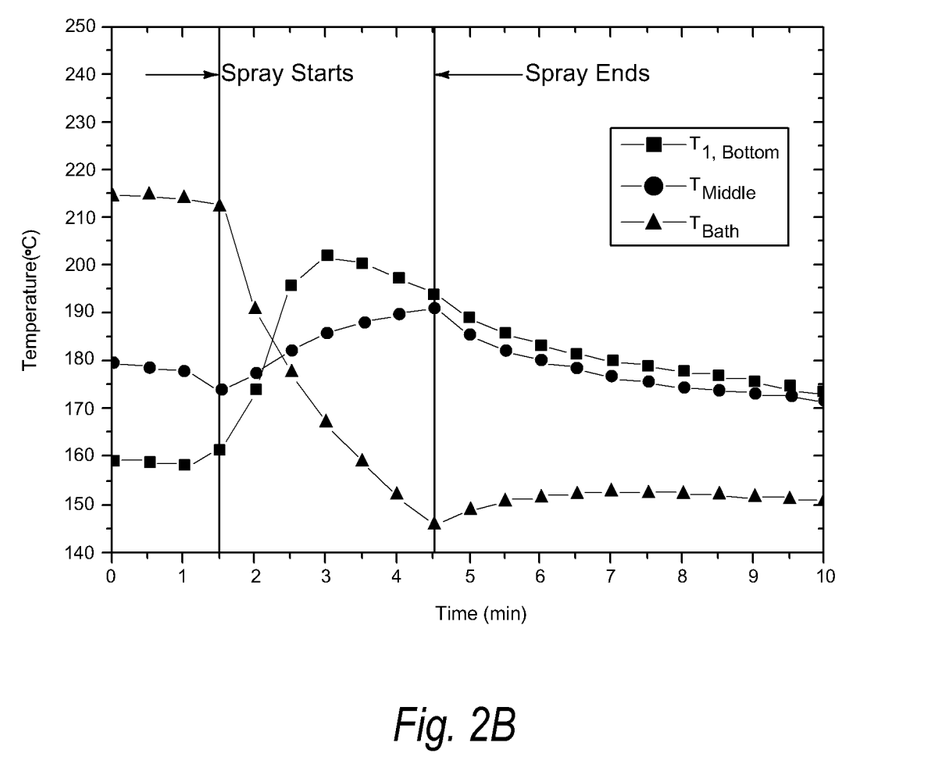
FIG. 2B is a graph of a temperature profile obtained with an oxidation reaction system having non-uniform temperature or a high temperature gradient across a cross-sectional profile of the reaction vessel.

From FIG. 2A, it is seen that both the bath and inlet temperatures decreased prior to the start of spraying by over 10° C. due to the heat transferred to the spray solution to raise its temperature from room temperature to nearly 200° C. Following the start of the spraying (after approximately 1 minute), the reactor temperatures increased by up to 20° C. This is attributed to the highly exothermic nature of the oxidation reactions. FIG. 2B shows the temperature profile in the reactor with only one heating block and a pre-heater with a lower heating capacity. Clearly, the temperatures range from 161° C. to 181° C. The bath temperature decreased about 70° C. during the spraying period. We attribute the loss of TPA yield and purity to large temperature gradients.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope. All references or publications recited herein are incorporated herein by specific reference.

The invention claimed is:

1. An oxidation process, comprising:
    combining small droplets of a liquid reaction mixture having an oxidizable reactant, a catalyst, and a solvent with oxygen and a diluent gas in a reaction zone, wherein the boiling point of the solvent is within the desired reaction temperature range for oxidizing the reactant to produce an oxidized product; and
    oxidizing the reactant with the oxygen to produce the oxidized product under controlled temperature and pressure conditions by maintaining the pressure conditions in the reaction zone such that the temperature of the droplets does not rise beyond the boiling point of the solvent at the pressure, whereby the latent heat of evaporation of the reaction mixture removes heat released by the reaction without the reaction mixture entirely evaporating; and
    wherein the temperature rise is not controlled by contacting the reaction mixture with a second liquid.

2. The process of claim 1, wherein the reaction temperature is controlled within a range of 100 to 300 degrees Celsius and the reaction pressure is controlled within a range of 1 to 100 atmospheres.

3. The process of claim 1, wherein a substantially uniform temperature and pressure are maintained throughout a reaction vessel in which the process is carried out.

4. The process of claim 2, wherein the liquid reaction mixture is preheated to within the reaction temperature range prior to combining the liquid reaction mixture with oxygen and a diluent gas in the reaction zone.

5. The process of claim 1, wherein the liquid reaction mixture is combined with oxygen and a diluent gas in the reaction zone by spraying the liquid reaction mixture into the reaction zone in the form of 0.1 micron to 1 mm droplets.

6. The process of claim 1, further comprising providing solvent vapor to the reaction zone prior to introducing the liquid reaction mixture into the reaction zone such that the liquid reaction mixture enters a vapor phase saturated with the solvent at the reaction temperature and pressure, thereby minimizing solvent evaporation from the liquid reaction mixture.

7. The process of claim 1, wherein the liquid reaction mixture and the oxygen have a contact time in the reaction zone such that burning of the solvent or other oxidizable components to form CO or $CO_2$ is inhibited.

8. The process of claim 1, wherein the solvent is selected so that the oxidized product precipitates from the droplets as a substantially pure solid material.

9. The process of claim 8, wherein the catalyst remains dissolved in the droplets as the reaction proceeds.

10. The process of claim 1, wherein an oxidation intermediate between the oxidizable reactant and oxidized product is added to the liquid reaction mixture.

11. The process of claim 10 wherein said oxidation intermediate is selected from the group consisting of p-toluic acid, p-tolualdehyde, p-hydroxymethyl benzoic acid, terephthaldehyde, 4-carboxybenzaldehyde, p-methylbenzyl alcohol, derivatives thereof, and mixtures thereof.

12. The process of claim 1, wherein the liquid reaction mixture includes an aromatic feedstock having an oxidizable substituent as the oxidizable reactant, and wherein the oxidized product is an aromatic compound having at least one carboxylic acid group.

13. The process of claim 12, wherein the aromatic feedstock includes a benzene ring having at least one oxidizable alkyl substituent, a furan hetero-ring having at least one oxidizable alkyl substituent, a naphthalene polyring having at least one oxidizable alkyl substituent or a derivative or mixture of any of these.

14. The process of claim 13, wherein the aromatic feedstock includes one or more of para-xylene, meta-xylene, ortho-xylene, pseudo-cumene, 3-chloro-meta-xylene, 2,6-dimethylnaphthalene, 1,5-dimethylnaphthalene, 2,7-dimethylnaphthalene, 5-hydroxymethylfurfural, furfural and 5-formylfurfural.

15. The process of claim 12, wherein:
the aromatic feedstock includes para-xylene and the aromatic compound having at least one carboxylic acid includes terephthalic acid; or
the aromatic feedstock includes 5-hydroxymethylfurfural or 2,5-dimethylfuran and the aromatic compound having at least one carboxylic acid includes furan-2,5-dicarboxylic acid.

16. The process of claim 14, wherein the liquid reaction mixture includes one or more of cobalt, manganese and bromine or hydrogen bromide.

17. The process of claim 1, wherein the solvent includes acetic acid and not more than 10 percent water.

18. The process of claim 1, wherein said controlled pressure and temperature conditions are such that the latent heat of vaporization of the reaction mixture provides enough heat capacity to maintain the reaction temperature at the phase change temperature of the reaction mixture without causing the reaction mixture to completely evaporate to limit the adiabatic temperature increase of reaction zone.

19. The process of claim 1, wherein the oxidized product precipitates from the droplets as a substantially pure solid material.

20. The process of claim 1, further comprising recovering the oxidized product from the reaction zone.

21. The process of claim 1, wherein the catalyst provided in the liquid reaction mixture includes one or more of the compounds of palladium, platinum, cobalt, manganese, vanadium, titanium, tin, antimony, bismuth and molybdenum dissolved in the liquid reaction mixture.

22. The process claim 1, wherein the diluent gas includes at least one of nitrogen or carbon dioxide.

23. The process of claim 1, wherein the liquid reaction mixture is contacted with oxygen in the reaction zone for a time period of about 0.1 seconds to about 60 minutes.

24. The process of claim 1, wherein the liquid reaction mixture and the oxygen have a contact time such that burning of the solvent or other oxidizable components to form CO or $CO_2$ is inhibited.

25. The process of claim 1, wherein the reactant conversion is greater than 95%.

26. The process of claim 1, wherein the process is conducted in a reactor and the reactor pressure is not adjusted in response to conversion measurements.

* * * * *